United States Patent [19]
Stewart et al.

[11] Patent Number: 5,316,860
[45] Date of Patent: May 31, 1994

[54] LEATHER TREATMENT SELECTED AMPHIPHILIC COPOLYMERS

[75] Inventors: Thomas Stewart, Doylestown; Patricia M. Lesko, Lansdale; Anton G. El A'mma, Phoenixville, all of Pa.

[73] Assignee: Rohm and Haas Company, Philadelphia, Pa.

[21] Appl. No.: 535,228

[22] Filed: Jun. 7, 1990

Related U.S. Application Data

[63] Continuation of Ser. No. 279,181, Dec. 2, 1988, abandoned.

[51] Int. Cl.$^5$ .......................... B32B 9/02; B32B 9/04
[52] U.S. Cl. .................... 428/473; 8/94.1 R; 8/94.21; 8/94.33; 427/389; 428/521; 428/522
[58] Field of Search .......... 8/94.1 R, 94.21, 94.23, 8/94.26, 94.27, 94.33, 436; 427/389; 428/473, 521, 522

[56] References Cited

U.S. PATENT DOCUMENTS

| | | | |
|---|---|---|---|
| 2,205,882 | 6/1940 | Graves | 149/5 |
| 2,205,883 | 6/1940 | Graves | 149/5 |
| 2,452,536 | 11/1948 | Kirk | 8/94.2 |
| 2,475,886 | 7/1949 | Goebel | 260/79.3 |
| 2,968,580 | 1/1961 | Plapper et al. | 117/135.5 |
| 3,010,780 | 10/1961 | Plapper et al. | 8/94.26 |
| 3,103,447 | 9/1963 | Lowell et al. | 8/94.19 |
| 3,231,420 | 1/1966 | Lowell et al. | 117/142 |
| 3,276,891 | 10/1966 | Heyden et al. | 106/287 |
| 3,423,162 | 1/1969 | Papayannis et al. | 8/94.19 |
| 3,945,792 | 3/1976 | Wurmli et al. | 8/94.21 |
| 3,968,148 | 7/1976 | Leister et al. | 260/486 |
| 4,009,195 | 2/1977 | Leister et al. | 260/46.5 |
| 4,314,800 | 2/1982 | Monsheimer et al. | 8/94.1 R |
| 4,314,802 | 2/1982 | Beier et al. | 8/94.26 |
| 4,327,997 | 5/1982 | Prentisse et al. | 8/94.26 |
| 4,345,006 | 8/1982 | Loechel et al. | 428/473 |
| 4,527,992 | 7/1985 | Friese et al. | 8/94.21 |
| 4,562,581 | 7/1985 | Prentisse et al. | 8/94.33 |
| 5,124,181 | 6/1992 | Schaffer et al. | 427/323 |

FOREIGN PATENT DOCUMENTS 0118706 6/1983 Poland .
265063 9/1967 U.S.S.R. .

OTHER PUBLICATIONS

*Leather Facts*, New England Tanners Club (1972).
*Leather Technician's Handbook*, J. H. Sharphouse, Leather Producers' Association (1971) chapters 21 and 24.
C. E. Retzche in "*An Aqueous System Destined for the Production of a Dry Cleanable Leather Which Is No Longer Wettable*" Rev. Tech. Ind. Cir., vol. 69 Issue 4 (1977).
"*Hydrophobing Leather*" The Leather Manufacturer, May 1986, pp. 11–14.

*Primary Examiner*—Michael Lusignan

[57] ABSTRACT

A method of improving the strength, temper and water resistance of leather utilizing selected amphiphilic copolymers is provided. The amphiphilic copolymers are formed from a predominant amount of at least one hydrophobic monomer and a minor amount of at least one copolymerizable hydrophilic monomer. The method is particularly useful as a one step substitute for conventional retanning and fatliquoring treatment steps. In a preferred embodiment the amphiphilic copolymers also provide a significant degree of water resistance to the leather.

14 Claims, No Drawings

LEATHER TREATMENT SELECTED AMPHIPHILIC COPOLYMERS

This application is a continuation of application Ser. No. 279,181, filed Dec. 2, 1988, now abandoned.

FIELD OF THE INVENTION

This invention is directed to the use of selected amphiphilic copolymers for treating leather, and more particularly to a method for treating tanned leather to improve strength, temper and water resistance while eliminating at least one conventional wet end leather processing step.

Background of the Invention

The treatment of hides and skins to form leather involves a number of interdependent chemical and mechanical operations. These operations may be divided into a sequence of wet end steps followed by a sequence of dry steps. A typical leather making process involves the following sequence of wet end steps: trimming and sorting, soaking, fleshing, unhairing, baiting, pickling, tanning, wringing, splitting and shaving, retanning, coloring, fatliquoring and setting out. These wet end steps are followed by a sequence of dry steps such as drying, conditioning, staking, buffing, finishing, plating, measuring and grading. A description of each of these operations is provided in *Leather Facts*, New England Tanners (1972).

The present invention is involved with the wet end operations which take place after primary tanning; namely retanning and fatliquoring. The object of primary tanning is to convert the hide or skin to a stable non-spoilable material. This is accomplished by converting raw collagen fibers in the hide or skin into a stable product which is non-putrescible or in other words will not rot. In addition, tanning improves a number of properties of the hide or skin such as for example, dimensional stability, abrasion resistance, resistance to chemicals and heat, improved flexibility, and the ability to endure repeated cycles of wetting and drying. The principal method used to tan hides and skins is known as "chrome tanning". This employs a basic chromium sulfate, often referred to simply as "chrome", which is prepared by the reaction of a chromium salt, like sodium bichromate, with a sugar-like substance and sulfuric acid. The chrome penetrates into the skin producing a bluish-green color. The color change is used to assess the extent of penetration or degree of tanning. In addition, the shrinkage temperature is used to measure the rate and degree of tanning. Untanned leather will shrink significantly when subjected to hot water, as for example 140° F. water, while properly chrome tanned leather can withstand higher temperatures, such as for example 212° F. water, without shrinking. For a description of chrome tanning see U.S. Pat. No. 4,327,997. Hides and skins may also be tanned using vegetable extracts for example extracts from trees and shrubs such as quebracho, wattle, sumac, hemlock, oak and spruce.

After tanning, the leather is retanned, colored and fatliquored. This three step operation is often considered together as one step since all three operations may be carried out sequentially in one drum. Chrome-tanned stock, also referred to as "blue stock", retains much of the uneven fiber structure pattern in the skin on the animal. Some areas of the skin possess a dense structure while other portions are loosely fibered and some portions may be undesirably thin and papery. Since the tanner desires to produce a uniform piece of leather, a second tanning step, known as "retanning", is employed to improve both aesthetic and physical properties. These properties include, for example, improvements to the fullness of the leather, the tightness and smoothness of the grain, the break, the levelness and intensity of the dye shade, better uniformity in temper or flexibility, better wettability and additional stability against water and perspiration. Retanning can be accomplished using a variety of naturally derived materials including extracts from vegetables or plants, and synthetic tanning agents known as "syntans", or combinations thereof. Historically, extracts from trees and shrubs like quebracho, wattle, sumac, hemlock, oak and spruce were used as retanning agents. Over the past 50 years many manmade syntans were developed and these are used extensively today, especially for manufacturing soft-leather and making white or pastel color leathers. Retanning is typically conducted at temperatures of from about 80° F. to about 120° F. using from about 3 to about 20 weight percent of retanning agent on the wet weight of the tanned leather. In some instances the hide may be chrome retanned before the regular retanning step to fully tan any previously untanned portions and to level out the chrome especially in the grain for more uniform dyeing. Retanning typically takes on the order of 1 to 2 hours, while the entire retanning, coloring and fatliquoring sequence usually takes from about 4 to 6 hours. After retanning the hide is colored using either a surface type dye or a penetrating dye. In general, acidic dyes penetrate through the hide while basic dyes are used to color only the surface.

After retanning and coloring the hide is then subjected to the fatliquoring step. Fatliquoring imparts the desired properties of strength and temper to the leather. The fatliquor lubricates the leather fibers so that after drying the fibers are capable of sliding over one another. In addition to regulating the pliability of the leather, fatliquoring contributes greatly to the tensile and tearing strength of the leather. Fatliquoring also affects the tightness of the break or in other words the crease pattern formed when the grain surface is bent inward; the object being to produce a leather which leaves no or few fine wrinkles when it is bent.

The basic ingredients used in fatliquoring are water insoluble oils and fatty substances such as raw oils and sulfated and sulfited oils. Typically the weight percent of fatliquor oil on weight of leather ranges from 3 to 10 percent. The manner in which the oil is distributed throughout the leather affects the character of the leather and subsequent finishing operations. To obtain a uniform oil coating over a large surface of leather fibers it is necessary to dilute the oil with an organic solvent or preferably to disperse the oil in an aqueous system using emulsifiers. See *Leather Technician's Handbook*, J. H. Sharphouse, Leather Producers' Association (1971) chapters 21 and 24.

While techniques directed to controlling the degree to which the emulsion penetrates the leather before breaking and depositing as oil on the fibers have been employed to make leathers softer and more flexible, long term water resistance or waterproofness has not been successfully accomplished using conventional fatliquors alone.

Description of the Prior Art

A number of publications have proposed various copolymers for treating leather during tanning and retanning, particularly as replacements for natural tanning agents and syntans formed from phenol-formaldehyde resins.

U.S. Pat. Nos. 2,205,882 and 2,202,883 disclose the use of acidic polymers such as polyacrylic acid; copolymers of acrylic acid and methacrylic acid; copolymers of maleic anhydride and styrene; copolymers of methacrylic acid and styrene; and hydrolyzed methyl methacrylate.

U.S. Pat. Nos. 2,475,886 and 2,452,536 disclose sulfonated water soluble, styrene-maleic anhydride copolymers for tanning or retanning leather.

U.S. Pat. No. 3,103,447 is directed to aqueous solutions of ammonium or amine salts of acid-containing copolymers for impregnating leathers to achieve the properties associated with retanned leather such as improved break, resistance to abrasion and fuller substance. The copolymers are disclosed to be insoluble in water in acid form, but soluble in the salt form in which they are used. The copolymers are formed from polymerizable monoethylenically unsaturated acids such as acrylic or methacrylic acid, with esters such as saturated monohydric aliphatic alcohol esters of acrylic or methacrylic acid obtained from cyclohexanol, alkanols having 1 to 18 carbon atoms or vinyl esters of fatty acids having 1 to 18 carbon atoms such as vinyl acetate, vinyl laurate and vinyl stearate. Preferred copolymers are those formed from 5 to 35 weight percent acrylic or methacrylic acid and 95 to 65 weight percent ester. Specifically exemplified copolymers include those formed from 85 weight percent ethyl acrylate and 15 weight percent methacrylic acid; 66 weight percent butyl acrylate and 34 weight percent acrylic acid; 60 weight percent methyl acrylate, 25 weight percent 2-ethylhexyl acrylate and 15 weight percent methacrylic acid.

U.S. Pat. No. 3,231,420 is directed to a process of impregnating leather with water insoluble copolymers to prepare the leather for finishing. This process is disclosed to improve break, provide fuller substance, and improve abrasion and scuff resistance; properties typically achieved by retanning. The copolymers used are formed from (a) 3.5 to 18.5 mole percent of an acid selected from acrylic acid, methacrylic acid and itaconic acid (b) from 1.5 to 8 mole percent of at least one ester of a (meth)acrylic acid and a saturated monohydric alcohol having 8 to 18 carbon atoms (c) from 10.5 to 43 mole percent methyl, ethyl or isobutyl methacrylate, and (d) from about 47 to 84.5 mole percent of an ester of acrylic acid with a saturated monohydric alcohol having 1 to 14 carbon atoms; the total concentration of (a) plus (c) being from 15 to 45 mole percent, and the ratio of (b) to (c) being from 1:3.3 to 1:6.7. The copolymer, having all four essential ingredients, is formulated in an organic solvent such as alcohols, ketones, esters, hydrocarbons and chlorinated hydrocarbons or mixtures thereof, a preference being for hydrophobic hydrocarbons and halogenated hydrocarbons which do not swell the leather and which permit impregnation.

U.S. Pat. No. 3,945,792 is directed to a process for filling tanned leather using unsubstituted or substituted homo- or copolymers of acrylic acid which are soluble in water in admixture with a protein glue in the ratio of polymer to protein glue of 1:12 to 12:1.

U.S. Pat. No. 4,314,802 discloses a multiple stage leather tanning process. The first step uses an aqueous solution or dispersion of a polymer containing at least 50 percent acrylic or methacrylic acid with an optional, minor amount of an alkyl ester of (meth)acrylic acid or a sulfated, unsaturated drying oil. The second step uses a zirconium tanning compound.

U.S. Pat. No. 4,345,006 is directed to methods for treating tanned leather with a hydrophilic acrylate resin in aqueous dispersion. The hydrophilic acrylate is a film forming copolymer formed from 60 to 80 weight percent (meth)-acrylate ester having a glass transition temperature (Tg) less than OOC such as for example ethyl acrylate; 10 to 20 weight percent of a hydroxyalkyl ester of (meth)acrylic acid; 1 to 10 weight percent of a polymerizable anionic compound such as itaconic, maleic, fumaric, crotonic, acrylic or methacrylic acid, preferably in the form of a water soluble alkali metal or ammonium salt; 0.2 to 2.5 weight percent of at least one crosslinking monomer; and from 0 to 2.5 weight percent (meth)acrylamide. The predominant (meth)acrylate component having a low Tg is generally described as being an ester of alcohols, preferably alkanols, having 2 to 18 carbon atoms. The compositions are hydrophilic film-forming coatings low in acid functional monomers (e.g. 10 to 20 weight percent hydroxy functional monomer) useful as retanning agents, but not disclosed as being substitutes for fatliquoring or as part of a waterproofing treatment.

U.S. Pat. No. 4,526,581 is directed to a tanning or retanning process using methacrylic acid copolymers of a narrow molecular weight range. The copolymers contain at least 5 mole percent of a short ($C_1$–$C_4$) chain alcohol ester of acrylic acid. The combination of methacrylic acid and short chain alcohol ester comonomer is stated as providing unexpected properties, as for example substantial resistance to grain cracking and detannage.

In addition a number of publications have separately addressed the problem of making treated leather more water resistant or completely waterproof. Some of these publications attempt to make the leather surface less hydrophilic by causing a chemical reaction with chrome or other mineral tanning agents in the leather, or by multiple treatments using acids and polyvalent metal salts.

U.S. Pat. No. 2,968,580 discloses impregnating leather with an aqueous solution of salts of acid esters having at least two salt forming acyl groups, drying the leather, and then reacting the acid with a water miscible complex salt of a polyvalent metal.

U.S. Pat. No. 31,010,780 uses a mineral tanning agent to form a complex with non-polymeric tribasic or higher polybasic acid derivatives containing hydrophobic groups such as for example, boric acid, phosphoric acid, arsenic acid, citric acid, trimesitinic acid, mellitic acid, ethanetetraacetic acid and the like.

U.S. Pat. No. 3,276,891 uses partial esters and partial amides of aliphatic polycarboxylic acids having 3 to 10 carbon atoms and 2 to 4 carboxylic acid groups; amino aliphatic polycarboxylic acids having 4 to 10 carbon atoms or phenyl or hydroxy phenyl polycarboxylic acids of 2 to 6 carboxylic acid groups, with partial esters and partial ethers of polyalcohols having 2 to 10 carbon atoms and at least two free hydroxy groups and one unsaturated $C_8$–$C_{22}$ lipophilic radicals as impregnants in an organic solvent.

Soviet Union Patent 265,063 entitled "Hydrophobic Treatment" discloses the use of a high molecular weight hydrophobe, which is the reaction product of an alkali metal glycolate with a styrene-maleic anhydride or polyacrylic acid copolymer, to enhance water repellence.

C. E. Retzche in "An Aqueous System Destined for the Production of a Dry Cleanable Leather Which Is No Longer Wettable" Rev. Tech. Ind. Cir., Vol. 69, issue 4 (1977) addresses the difficulty in making leathers, which have been treated with hydrophilic syntans and fatliquors, water resistant. Retzche proposes the use of certain phosphatecontaining polymers in combination with a chrome compound.

U.S. Pat. No. 4,527,992 is also directed to a process for producing waterproof leathers and skins by treating tanned hides with a stuffing agent selected from oxidized $C_{18}$-$C_{26}$ aliphatic hydrocarbons, oxidized and partially sulfonated $C_{18}$-$C_{26}$ aliphatic hydrocarbons, oxidized $C_{32}$-$C_{40}$ waxes and oxidized and partially sulfonated $C_{32}$-$C_{40}$ waxes. This stuffing agent treatment is followed by the use of impregnating agents in the form of an alkali metal or ammonium or lower alkyl amine salt copolymers of from 60 to 95 mole percent of an unsaturated acid selected from acrylic and methacrylic acid and from 5 to 40 mole percent of a monomer selected from methyl acrylate, ethyl acrylate, propyl acrylate, butyl acrylate, acrylamide, acrylonitrile, methyl methacrylate, ethyl methacrylate, propyl methacrylate, butyl methacrylate, methacrylamide and methacrylonitrile, where the copolymer has a molecular weight of from 800 to 10,000. This treatment is followed by acidification, fixing and finishing.

These numerous publications, employing various combinations of hydrophilic and hydrophobic monomers, demonstrate that no one has heretofore found a material useful for treating tanned leather in one step to provide the properties desired by the wet end steps of retanning, fatliquoring and waterproofing.

It is an object of the present invention to provide a copolymer useful for treating tanned leather in one step so as to yield the desired combination of properties desired by conventional wet end retanning and fatliquoring steps.

It is an additional object of the invention to provide a copolymer which also improves the water resistance of leather.

It is a further object of the present invention to provide a copolymer which can also improve the intensity of dye shade, resistance to solvent extraction, washability, and waterproofness of leather and which reduces the drying time and energy required at the end of the wet end processing.

SUMMARY OF THE INVENTION

A process for treating tanned leather to improve aesthetics, strength and temper is provided. The process involves the use of water dispersible, selected amphiphilic copolymers formed from a predominant amount of at least one hydrophobic monomer and a minor amount of at least one hydrophilic copolymerizable monomer. In a preferred embodiment the selected amphiphilic copolymer is demonstrated to be an effective one step treatment substitute for conventional retanning and fatliquoring steps, and in another embodiment the selected copolymer is shown to also improve the water resistance of the treated leather.

DETAILED DESCRIPTION OF THE INVENTION

We have found that aqueous dispersions of water insoluble amphiphilic copolymers formed from a predominant amount of at least one hydrophobic monomer and a minor amount of at least one copolymerizable hydrophilic comonomer are useful for treating tanned leather during wet end processing to achieve a number of desirable aesthetic and physical properties.

The amphiphilic copolymer contains both hydrophilic and hydrophobic groups. The copolymer is formed from greater than 10 percent by weight to less than 50 percent by weight of at least one hydrophilic monomer and greater than 50 percent by weight to less than 90 percent by weight of at least one hydrophobic comonomer.

The selection of the relative concentration of hydrophilic to hydrophobic monomers used for preparing the amphiphilic copolymers is the result of empirical testing of the copolymers compared with controls using selected performance criteria or targets. The illustrative examples presented hereinafter clearly demonstrate that comparative amphiphilic copolymers, prepared from 10 weight percent of the hydrophilic monomer and 9.0 weight percent of the hydrophobic comonomer, do not meet these performance targets; especially temper and water resistance. Likewise, when the copolymer is formed from equal (50/50) weight concentrations of the hydrophilic monomer and hydrophobic monomer these performance targets are also not met.

The hydrophilic monomer used to prepare the amphiphilic copolymer is at least one monomer selected from water soluble ethylenically unsaturated, preferably monoethylenically unsaturated, acidic or basic monomers or mixtures thereof. Examples of suitable hydrophilic monomers include acrylic acid; methacrylic acid; itaconic acid; fumaric acid; maleic acid and anhydrides of such acids; acid substituted (meth)acrylates such as, for example, phosphoethyl methacrylate and sulfoethyl methacrylate; acid substituted (meth)acrylamides such as, for example, 2-acrylamido-2-methylpropylsulfonic acid; and basic substituted (meth)acrylates and (meth)acrylamides such as, for example, amine substituted methacrylates including, dimethylaminoethyl methacrylate, tertiarybutyl-aminoethyl methacrylate and dimethylaminopropyl methacrylamide and the like. A preferred water soluble hydrophilic monomer used to prepare the amphiphilic copolymer is acrylic acid.

The selection of the nature and concentration of the hydrophilic monomer was made to impart the amphiphilic copolymer with the ability to be well dispersed in an aqueous solution, and for it to be prepared at high polymer solids at a handleable or shearable viscosity without adversely affecting the ability of the copolymer to penetrate leather and provide it with improved aesthetics, strength, temper, and water resistance.

The hydrophobic comonomer used to prepare the amphiphilic copolymer is at least one monomer selected from long chain alkyl(meth)acrylates, long chain alkoxy(polyethyleneoxide) (meth)acrylates, alkylphenoxy(polyethyleneoxide) (meth)acrylates, primary alkenes, and vinyl esters of long chain alkyl carboxylic acids, and mixtures thereof. Suitable hydrophobic monomers include $C_8$-$C_{22}$ alkyl acrylates, $C_8$-$C_{22}$ alkyl methacrylates; $C_8$-$C_{22}$ alkoxy or $C_6$-$C_{12}$ alkyl phenoxy(polyethylene oxide) (meth)acrylates; $C_{12}$-$C_{22}$ 1-alkenes, and vinyl esters of $C_{12}$-$C_{22}$ alkyl carboxylic acids. Examples of such hydrophobic monomers include dodecyl (meth-)acrylate, pentadecyl (meth)acrylate, cetyl (meth)acrylate, stearyl (meth)acrylate, eicosyl (meth)acrylate, isodecyl (meth)acrylate, vinyl stearate, nonylphenoxy(ethyleneoxide)$_{1-20}$ (meth)acrylate, octadecene, hexadecene, tetradecene, dodecene, and mixtures of any of the above.

The preferred hydrophobic monomers found to provide the amphiphilic copolymer with the best performance characteristics, particularly in terms of water resistance, are of long chain ($C_{12}-C_{20}$) alkyl (meth)acrylates and mixtures thereof, such as mixtures of $C_{16}-C_{20}$ alkyl methacrylates (referred to hereinafter as "CEMA" for cetyleicosyl methacrylate. The use of the terminology (meth) followed by another term such as acrylate or acrylamide, as used throughout the disclosure refers to both acrylates or acrylamides and methacrylates or methacrylamides, respectively.

Minor amounts, of other ethylenically unsaturated copolymerizable monomers at concentrations equal to or less than 50 weight percent of the total hydrophobic comonomer concentration, may be used in combination with a predominant amount greater than about (50 weight percent) of at least one of the above types of hydrophobic monomers. These additional hydrophobic comonomers have been found to be useful as diluents for the other hydrophobic comonomers without adversely affecting the retan/fatliquor properties obtained upon treatment of the leather with the amphiphilic copolymer. The use of such diluents for the hydrophobic monomer may be justified by economics; however, improvements in water resistance obtained using the predominant hydrophobic monomer may be sacrificed by use of such diluent hydrophobes. Examples of such useful copolymerizable hydrophobic diluent comonomers include lower ($C_1-C_7$) alkyl (meth)acrylates, styrene, alpha-methyl-styrene, vinylacetate, (meth)acrylonitrile and olefins. When such hydrophobic diluents comonomers are employed, it is preferable to use unfunctionalized monomers rather than functionalized monomers, such as for example hydroxyl and amide functionalized monomers.

The amphiphilic copolymer may be prepared by the polymerization of the hydrophilic and hydrophobic monomers by any conventional technique. We have found a preference for conducting the polymerization in a water miscible alcohol such as, for example, tert-butanol or butyl Cellosolve ® using a water insoluble free radical initiator at a concentration of about 0.2% weight percent to about 5 weight percent on total monomers. Examples of suitable free radical initiators which may be used include peresters and azo compounds. The polymerization is preferably conducted at a temperature in the range of from 60° C. to about 150° C., preferably at a temperature of about 85° C. to about 120° C. Chain transfer agents such as mercaptans, may optionally be used to control molecular weight. Polymerization may be conducted by polymerizing all monomers together or by gradual addition of monomers and initiator over a period of from 1 to 6 hours until polymerization is essentially complete (greater than about 98% conversion). The polymerization produces a concentration of amphiphilic polymer solids in solvent of from as low as about 20% solids to as high about as 75% solids with a Brookfield viscosity of from about 100 to about 1,000,000 Cps.

Copolymers formed using olefinic hydrophobic monomers may be prepared according to the procedures, disclosed in U.S. Pat. Nos. 3,968,148 and 4,009,195 which are hereby incorporated by reference.

The amphiphilic copolymers exemplified in the illustrative examples presented hereinafter were made according to one of the following processes (A to D).

Process A

All charges were based on 1000 grams (g) monomer. The process is illustrated for making a 40 weight percent acrylic acid/60 weight percent CEMA copolymer. To a 4 necked 3 liter round bottomed flask equipped with a stirrer, thermometer, reflux condenser and blanketed with nitrogen was added 900 grams of tertiary butanol. The flask was then heated to 85° C. The following monomers: 400 g acrylic acid and 600 g cetyleicosyl methacrylate, along with 10 g Vazo 67 free radical initiator and 20 g 3-mercaptopropionic acid in 165 g deionized water as a chain transfer agent (CTA) were added evenly at a constant rate to the flask over 2 hours keeping the reaction at a temperature of 85° C. throughout. This was followed by the addition of 1 g Vazo 67 in 5 g t-butanol and the reaction was held at 85° C. for 1 additional hour. The reaction vessel was then cooled and the product copolymer was poured into a jar. The copolymer product had 48.1 wt % theoretical solids and 51.2 wt % observed solids and a weight average molecular weight of 10,600 and number average molecular weight of 6,500.

Process B

All charges were based on 200 grams of monomer. This process is illustrated to prepare a 70 wt % CEMA/30 wt % 2-sulfoethyl methacrylate copolymer. The reaction flask was the same as in Process A, except that it was 1 liter in volume. To the flask was added 150 g isopropanol and the flask was heated to 82° C. The following monomer mixture, initiator and chain transfer agent feeds were added linearly and uniformly to the heated flask (82° C.) over 2 hours. The monomer mixture was 200 g isopropanol, 140 g CEMA, 60 g 2-sulfoethyl methacrylate, and 2 g Vazo 67 initiator. The CTA was 2 g 3-mercaptopropionic acid and 25 g isopropanol. At the end of feeding the monomer mixture, initiator and CTA, 1 g Vazo 67 and 10 g isopropanol were added to the reaction vessel which was held at a temperature of 82° C. for 1 additional hour. At the end of this hour the reaction was cooled and the product poured into a jar. The copolymer product had a 34.7 wt % theoretical solids and 34.3 wt % observed solids. The weight average molecular weight was 13,000 and the number average molecular weight of 9,660.

Process C

This process was carried out according to the disclosure in U.S. Pat. No. 3,968,148 and U.S. Pat. No. 4,009,195. It is illustrated for making a copolymer of 35 wt % acrylic acid and 65 wt % hexadecene. To a 1 liter round bottomed 4 necked flask equipped with a stirrer, thermometer, reflux condenser and blanketed with nitrogen was added 450 grams of hexadecene. The flask was then heated to 130° C. A feed of 120 g acrylic acid, 30 g hexadecene and 3 g t-butyl perbenzoate initiator was then linearly and uniformly added to the flask over 5 hours while maintaining the temperature at 130° C. The temperature was maintained at 130° C. for 1 hour and then cooling was begun and a diluent of 150 g butyl Cellosolve ® (2-butoxyethanol) was added. The copolymer formed had 46.2 wt % total solids in butyl Cellosolve ® with some residual hexadecene.

Process D

Polymers used for a molecular weight ladder (example 5) were prepared according to Process A with the exception that the amount of 3-mercaptopropionic acid (3 MPA) (chain transfer agent or CTA) was varied as followed. All charges are in grams.

| Monomers | | | Molecular Weight | |
| --- | --- | --- | --- | --- |
| AA | CEMA | 3 MPA | MW | MN |
| 300 | 700 | 0 | 69,000 | 24,200 |
| 300 | 700 | 2.5 | 25,100 | 16,500 |
| 300 | 700 | 6 | 16,650 | 11,300 |
| 300 | 700 | 20 | 10,000 | 6,500 |
| 300 | 700 | 40 | 4,500 | 3,400 |
| 300 | 700 | 60 | 3,000 | 2,400 |

Evaluation of Copolymers

The process of the present invention involves the treatment of leathers with the selected amphiphilic copolymers. We evaluated the amphiphilic copolymers by comparing the aesthetics, strength, flexibility, elasticity and water resistance of leathers treated with the amphiphilic copolymers with the same leathers treated with conventional syntan retanning agents and fatliquors. The strength of the treated leather was measured by a technique called elongation at grain crack and elongation at ball burst. This technique is commonly used in the art to evaluate the effectiveness of conventional fatliquors to lubricate the leather. The test is designed to reproduce the stretching of leather over a last during shoemaking, using an instrument called a Lastometer. A strip of treated leather is clamped in place and a probe then stretches the leather. The extension of the leather under the force of the probe is measured in millimeters at the point when a crack is first observed in the grain ("grain crack") and at the point where the leather tears ("ball burst"). The greater the extension at grain crack and ball burst, the greater the tear strength of the leather. For the purpose of evaluating the effectiveness of the amphiphilic copolymers, we established criteria for extension at grain crack and ball burst of 5 ounce (oz.) chrome tanned cowhide of greater than or equal to 13 mm and greater than or equal to 15 mm, respectively, as being the minimum value for strength improvement by the treatment. In addition to evaluating the improvement in leather strength achieved by the application of the amphiphilic copolymers, we also quantitatively evaluated the temper of the leather and compared this with temper measurements obtained by treatment with conventional retanning and fatliquoring agents. Temper is a measure of the flexibility and elasticity of leather, the higher the temper, the better the leather's flexibility and elasticity. We measured the temper of treated leather samples using a Hunter-Spring compression tension tester modified according to Stubbings: Stubbings and E. Senfelder, JALCA, Vol. 58, No. 1, Jan. (1963), and established as a minimum criterion a temper value of at least 155 mils.

In addition to the quantitative evaluation of strength and temper, we also qualitatively observed the break characteristics of the treated leather.

Furthermore, we also evaluated the dye shade intensity for conventionally treated and chrome tanned leather samples versus chrome tanned leathers treated with the amphiphilic copolymers. The higher the dye shade intensity, the more intense the dye shade on the leather for a given weight percent dye offer (used).

We noticed that leathers treated with the amphiphilic copolymers of the invention resulted in faster drying time during subsequent operations. This improvement in drying time, along with the ability to eliminate at least one conventional wet end processing step, provides additional economics and energy conservation characteristics to the present invention.

In a preferred embodiment of the invention, we unexpectedly found that treating leathers with the selected amphiphilic copolymers not only improved the above physical and aesthetic properties of leather, but also had the ability to improve the water resistance of the treated leather and that, if the leather treated with the amphiphilic copolymer was subsequently treated with a mineral tanning agent, the resulting leather meets the requirements of a waterproof leather product. As used herein the term "waterproof" does not mean that the leather could never absorb water or be penetrated by water under any conditions, but rather is used to convey a higher degree of water resistance than the term "water resistant", as used herein, implies.

The water resistance of leathers treated with the amphiphilic copolymer and controls was determined by two separate tests. The first is called a dynamic saline water resistance test. This test uses a Maeser water penetration tester according to ASTM D-2009-70. The number of Maeser flexes needed to cause water to penetrate the leather is recorded. Since this test utilizes saline water, it is useful for predicting the resistance of leather to damage not only from water, but also from perspiration. A Maeser flex value of greater than 15,000 is the minimum criterion established by the U.S. military for waterproof boot leather.

Treated leathers were also evaluated by a static water absorbance test by which samples of the leathers treated with the amphiphilic copolymer were immersed in water for two hours at room temperature, and the leather was then reweighed to determine the percent water uptake by the leather. The lower the percent water uptake, the more resistant the leather is to water. The military specification for water uptake by static water absorption is less than or equal to 30%.

The evaluation of the amphiphilic copolymers for treating tanned leathers (procedure F) was compared with a control process used with conventional retanning agents and fatliquors (procedure E). Unless otherwise noted, all leathers were prepared from 5 ounce (stock weight) chrome tanned cowhides. The procedures are applicable, however, to the other types of hides and skins such as chrome tanned pigskin, chrome tanned sheepskin, vegetable tanned sheepskin and the like.

Procedure E: Control

All weights are based on the weight of the blue stock (i.e. 100% means a weight equal to the weight of the stock in the drum).

1) The stock was given a ten minute open-door water wash at 32° C.

2) To this was added 200% float (float refers to water: 200% float means the addition of twice the amount of water to stock weight) at 32° C. and then 1% Neutralizing Agent ® and 1% ammonium bicarbonate. The mixture was then drummed (mixed) for 120 minutes.

3) The drum was then drained and the stock was given a 10 minute open door water wash at 55° C.

4) To this was added 100% float at 46° to 54° C.

5) The conventional retanning agent used as the control (6.6% Leukotan ® 974 at 30% solids equal to 2% active Leukotanlo) was diluted with an equal weight of water and added to the drum mixture through the gudgeon (drum opening). The mixture was then drummed for 60 minutes.

6) An acid dye (0.5% Derma Orange 2R predissolved in hot water) was then added to the drum and the mixture was drummed for 20 minutes.

7) One percent formic acid (prediluted to a 10% solution) was then added to fix the dyed stock.

8) The drum was drained and the stock was washed with water for 10 minutes with the door open at 35° C.

9) To this was added 100% float at 55° C., and then the fatliquor (6% Moritel ® G-82 sulfated fatliquor (70% active)) dispersed in 20% water at 55° C. was added followed by drumming the mixture for 40 minutes.

10) 0.5% formic acid was then added to fix and the stock was then drummed for 10 minutes and then drained.

11) This step was an optional step involving post-treatment with a mineral tanning agent. In this case, chromium was used. A solution prepared from 100% float, 3% Tanolin ® M-1 and 0.5% formic acid, prepared 0.5 to 4 hours before use, was added and drummed for 60 minutes at 35° C.

12) The stock was washed for 10 minutes with the door open at 27° C.

13) The stock was then horsed (stored in a pile) overnight.

14) The stock was then set out ( to smooth and remove excess moisture) and vacuum dried for 2 minutes at 70° C.

15) The stock was then aired off (hung to dry) overnight and conditioned for 1-7 days in a constant temperature room at 72° F., 60% relative humidity and then staked (mechanically softened).

Procedure F

This procedure was used with the one step retanning and fatliquoring amphiphilic copolymers of the invention. All weights are based on the weight of the blue stock or other tanned hide.

1) The stock was given a 15 minute open door water wash at 40° C.

2) To this was added 200% float at 40° C. followed by the addition of 1% Neutralizing Agent ® and 1% ammonium bicarbonate and the mixture was drummed for 120 minutes.

3) The drum was then drained and the stock was then given a water wash for 15 minutes with the door open at 50° C.

4) The copolymer was predispersed by first adding to the float either sodium hydroxide (in the case where the copolymer was formed from an acidic hydrophilic monomer) or formic acid (in the case where the copolymer was formed from a basic hydrophilic monomer) in an amount sufficient to neutralize at least 50% of the polymeric acid or base as was the case. The copolymer was then dispersed in 100% float by vigorous agitation with either a magnetic stirring bar or a blade stirrer. The amphiphilic copolymer so predispersed in 100% float was then added and the mixture was drummed for 60 minutes at 50° C. The amphiphilic copolymer was charged at 6 wt % on the stock weight unless otherwise indicated.

5) To this was added an acidic dye (0.5% Derma Orange 2R predissolved in hot water) and drummed for 20 minutes at 50° C.

6) One percent formic acid (10% solution) was added to fix when an acidic hydrophilic comonomer was used (and one percent sodium bicarbonate when a basic hydrophilic comonomer was used), and the mixture was drummed for 10 minutes at 50° C.

7) The drum was drained and the stock was washed for 15 minutes with the door open at 35° C.

8) This step (like step 11 in Procedure E) is an optional step involving post treatment with a mineral tanning agent, in this case chromium. A solution prepared from 100% float, 3% Tanolin ® M-1 and 05.% formic acid (prepared 0.5 to 4 hours before use) was added to the stock and drummed 60 min. at 35° C.

9) The stock was then washed for 15 minutes with the door open at 35° C.

10) The stock was then horsed overnight.

11) The stock was then set out and vacuum dried for 2 minutes at 70° C.

12) The stock was then aired off overnight and conditioned for 1-7 days in a constant temperature room (72° F., 60% relative humidity) and then staked.

Note that Procedure F, used to retan and fatliquor the tanned hides using the amphiphilic copolymers of the invention, required only 12 steps as compared with 15 steps for the conventional procedure; eliminating a fixation and a wash step and a separate fatliquor addition step.

The following examples are presented to illustrate the invention and the results obtained by the test procedures. The examples are illustrative only and are not intended, nor should they be construed, to limit the scope of the invention as modifications should be obvious to those of ordinary skill in the art.

EXAMPLE 1: LEATHER TREATMENT

This example compared the process of the invention for treating leathers with the amphiphilic copolymer to leathers prepared with conventional retans and fatliquors. In each case, a 5 oz. chrome tanned blue stock was used as the substrate. Leathers treated with effective amounts of the amphiphilic copolymer met or exceeded targeted performance properties including, fullness (thickness ratio), break, temper and strength (elongations at ball burst and grain crack) and dye shade intensity, and are superior to conventionally treated leather in water resistance. Procedure F also has the advantage of requiring fewer steps than procedure E.

TABLE 1

A Comparison of the Treatment Process Using the Selected Amphiphilic Polymers with a Conventional Retan and Fatliquor

| Sample Number | Materials Added | Dynamic Water Resistance Maeser Flex[1] | Static Water Resistance wt % uptake[2] | Break[3] | Temper[4] (mils) | Extensions[5] | | TR[9] | Dye[10] Shade |
|---|---|---|---|---|---|---|---|---|---|
| | | | | | | Grain Crack | Ball Burst | | |
| | Targets | | | | | | | | |

TABLE 1-continued

A Comparison of the Treatment Process Using the Selected
Amphiphilic Polymers with a Conventional Retan and Fatliquor

| Sample Number | Materials Added | Dynamic Water Resistance Maeser Flex[1] | Static Water Resistance wt % uptake[2] | Break[3] | Temper[4] (mils) | Grain Crack | Ball Burst | TR[9] | Dye[10] Shade |
|---|---|---|---|---|---|---|---|---|---|
| | strength, break | | | good | ≧155 | ≧13 | ≧15 | | |
| | waterproof | >15,000 | <30 | | | | | | |
| | water resistant | >1,000 | <70 | | | | | | |
| | *Leathers prepared by Procedure E* | | | | | | | | |
| [7]Comp. 1 | none | 50 | 93 | good | 133 | 12 | 13 | 1.0 | 5 |
| Comp. 2 | 3% Cr[8] | 50 | 97% | good | 133 | 11 | 13 | 1.0 | 4.5 |
| Comp. 3 | 2% L-974[8] | 20 | 116 | very good | 133 | 11 | 14 | 1.0 | 2.5 |
| Comp. 4 | 2% L-974, 3% Cr (Step 11) | 40 | 114 | fair | 137 | 11 | 14 | 1.0 | 2.0 |
| Comp. 5 | 4% G-82 | 200 | 111 | good | 175 | 13 | 15 | 1.0 | 4.5 |
| Comp. 6 | 4% G-82/3% Cr (Step 11) | 200 | 102 | good | 171 | 13 | 15 | 1.0 | 4.5 |
| Comp. 7 | 2% L-974/4% G-82/3% Cr (Step 11) | 300 | 107 | fair | 184 | 13 | 15 | 1.1 | 1.5 |
| | *Leathers prepared by Procedure F* | | | | | | | | |
| 1 | 2% Amph. | 4,000 | 66 | good | 160 | 12 | 15 | 1.1 | 4.0 |
| 2 | 2% Amph/3% Cr (Step 8) | 98,000 | 66 | good | 179 | 15 | 17 | 1.1 | 4.5 |
| 3 | 4% Amph/3% Cr (Step 8) | 84,000 | 32 | good | 228 | 15 | 22 | 1.1 | 3.5 |
| 4 | 6% Amph/3% Cr (Step 8) | 96,000 | 29 | good | 204 | 15 | 18 | 1.1 | 3.0 |

FOOTNOTES FOR TABLE 1
[1]Dynamic Water Resistance was measured on a Maeser Water Penetration Tester according to ASTM D2099-70 (reapproved in 1984.) The instrument used was manufactured by Koehler Instrument Co. of New York. Value is cycles to failure by water penetrating the leather. >15,000 flex cycles is the U.S. military specification for waterproof boot leather.
[2]Static water absorption: a 4 inch × 4 inch piece of leather was weighed and placed in water at room temperature for 2 hours. The piece was then reweighed and the percent increase in weight was recorded. Specification for U.S. military boot leather is 30% or less.
[3]Break: The break of the leather is the pattern of tiny wrinkles formed on the grain surface when it is bent grain inward. A pattern of no or few fine wrinkles is preferred over one of coarse wrinkles. Break was assessed qualitatively by those skilled in the art.
[4]Temper: a measure of the flexibility and elasticity of the leather. Temper was measured on a Hunter-Spring Compression Tension Tester, modified according to Stubbings: Stubbings and Eisenfelder, JALCA, Vol. 58, No. 1, January 1963. Measurement is in mils, the higher the value the more lubricated the material.
[5]A determination of the strength or lubrication of the leather. The test is designed to reproduce the stretching of leather over a last during shoe making. The instrument is called a Lastometer. A strip of leather is clamped in place, then a probe stretches the leather. The extension is measured in millimeters at the point when grain cracking is first observed (extension at grain crack), and at the point where the leather tears (ball burst). The greater the extension at grain crack and ball burst, the greater the tear strength of the leather.
[6]≧ means greater than or equal to.
[7]Comp. (Comparative Sample: (This abbreviation is used in subsequent examples)).
[8]Cr was Tanolin M-1 ®, a commercial product from Hamblett and Hayes: a 33% basic chrome sulfate powder containing an equivalent of 25% $Cr_2O_3$ (chromic oxide).
L-974 was Leukotan 974 ®, a commercial acrylic retanning agent (aka auxilliary tanning agent)
Morite G-82 was a commercial sulfated fatliquor.
Amph. was the amphiphilic copolymer = 70/30 w/w CEMA/AA (Synthesis A). All charges are wt % active ingredient as charged on the weight ot the chrome tanned stock.
[9]TR = thickness ratio, which is a measure of fullness. TR is the ratio of the crust thickness after treatment with retans and fatliquors (or amphiphilic copolymer) to the thickness of the wet blue stock before treatment.
[10]DS = dye shade intensity. Rated on a scale of 5 = strong dye shade to 1 = weak dye shade. A more intense dye shade for a given wt % dye charged to the leather demonstrates efficiency and is economically advantageous.

EXAMPLE 2: AMPHIPHILIC COPOLYMER COMPOSITION

This example demonstrates the treatment process utilizing selected amphiphilic copolymers prepared from various ratios of hydrophobic (CEMA) and hydrophilic (AA) monomers in terms of targeted properties: temper, strength and water resistance.

All the polymers illustrated in this example were synthesized according to Process A. All leathers were treated according to Procedure F, using 6 wt % copolymer solids on the weight of the blue stock, and using the optional chrome post treatment step.

The example shows the advantages of copolymer compositions containing greater than about 10 wt % to less than about 50 wt % hydrophilic monomer and greater than about 50 wt % to less than about 90 wt % hydrophobic monomer.

TABLE 2

Amphiphilic Syntan Compositions.
Effect of The Level of Hydrophilic Monomer

| Sample Number | Composition[1] Wt % AA | Wt % CEMA | Dynamic Water Resistance Maeser Flexes | Static Water Resistance Wt % Uptake | Temper (mils) | Grain Crack | Ball Burst |
|---|---|---|---|---|---|---|---|
| Targets | | | | | | | |
| Fatliquored leather | | | | | ≧155 | ≧13 | ≧15 |
| waterproof leather | | | >15,000 | <30 | | | |
| water resistant leather | | | >1,000 | <70 | | | |
| Comp. 1 | 70 | 30 | 30 | 108 | 128 | 11 | 13 |
| Comp. 2 | 60 | 40 | 100 | 75 | 101 | 9 | 15 |
| Comp. 3 | 50 | 50 | 219 | 51 | 109 | 9 | 16 |
| 5 | 48 | 52 | 5,600 | 54 | 167 | 12 | 17 |
| 6 | 45 | 55 | 23,500 | 56 | 179 | 13 | 16 |
| 7 | 40 | 60 | 89,600 | 26 | 204 | 14 | 21 |
| 8 | 30 | 70 | 121,300 | 22 | 224 | 16 | 20 |
| 9 | 30 | 70 (repeat) | 116,900 | 25 | 213 | 14 | 22 |
| 10 | 20 | 80 | 116,700 | 24 | 214 | 14 | 19 |

TABLE 2-continued

Amphiphilic Syntan Compositions.
Effect of The Level of Hydrophilic Monomer

| Sample Number | Polymer Wt % AA | Composition[1] Wt % CEMA | Dynamic Water Resistance Maeser Flexes | Static Water Resistance Wt % Uptake | Temper (mils) | Extensions Grain Crack | Ball Burst |
|---|---|---|---|---|---|---|---|
| 11 | 15 | 85 | 119,700 | 29 | 172 | 14 | 16 |
| 12 | 12 | 88 | 50,660 | 29 | 167 | 12 | 17 |
| Comp. 4 | 10 | 90 | 651 | 69 | 137 | 12 | 17 |
| Comp. 5 | 5 | 95 | 336 | 82 | 120 | 11 | 14 |

[1]AA = acrylic acid,
CEMA = cetyl-eicosyl methacrylate, a mixture of $C_{16}$, $C_{18}$ and $C_{20}$ methacrylic acid esters.

EXAMPLE 3: OTHER HYDROPHOBES

This example shows the results of treating leathers with the selected amphiphilic polymer compositions prepared with a variety of the selected hydrophobic monomers. The composition of all materials was 30 wt % AA and 70 wt % of the selected hydrophobe as indicated. Table 3 demonstrates the usefulness of some of the various selected hydrophobic monomers which may be used, and the advantages of the process of this invention using such polymeric compositions over conventional compositions (i.e., Styrene/acid or BMA/a-cid). Relative to the comparative polymeric compositions, the compositions of this invention demonstrated improvements in the strength of the leather (temper and extensions at grain crack and ball burst), as well as in the water resistance properties of the leather.

EXAMPLE 4: ADDITIONAL DILUENT COMONOMERS

This example demonstrates the performance of the process using additional selected amphiphilic copolymer compositions namely those containing at least one additional diluent monomer (butyl acrylate). These compositions had greater than 10% and less than 50% of a selected hydrophilic monomer; at least half of the remaining monomers being one of the selected hydrophobic monomers illustrated in Table 3 with the balance being another non-functionalized ethylenically unsaturated monomer (diluent (butylacrylate (BA)). All leathers were prepared according to Procedure F, using the optional chrome post treatment (Step 8).

TABLE 3

Variations in the Hydrophobic Monomer

| Sample Number | Polymer Comp. | Polymer Synth. Process | Dynamic Water[1] Resistance Maeser Flexes | Static Water[1] Resistance wt % Uptake | Temper[1] (mils) | Extensions[1] Grain Crack | Ball Burst |
|---|---|---|---|---|---|---|---|
| | Targets | | | | | | |
| | Fatliquored leather | | | | ≧155 | ≧13 | ≧15 |
| | waterproof leather | | >15,000 | <30 | | | |
| | water resistant leather | | >1,000 | <70 | | | |
| Comp. | styrene | A | 100 | 72 | 136 | 11 | 16 |
| | butyl methacrylate | A | 108 | 77 | 152 | 12 | 15 |
| 13 | 2-ethylhexyl acrylate | A | 6,000 | 28 | 194 | 13 | 16 |
| 14 | isodecyl methacrylate | A | 36,530 | 33 | 177 | 13 | 16 |
| 15 | lauryl acrylate | A | 120,700 | 28 | 247 | 14 | 21 |
| 16 | $C_{12}$–$C_{14}$ linear methacrylate | A | 64,800 | 26 | 198 | 14 | 19 |
| 17 | $C_{12}$–$C_{15}$ branched methacrylate | A | 36,400 | 29 | 202 | 13 | 19 |
| 18 | $C_{16}$–$C_{20}$ mixed methacrylate | A | 99,100 | 28 | 221 | 16 | 18 |
| 19 | nonylphenoxy $(EO)_4$ methacrylate | A | 700 | 43 | 180 | 13 | 16 |
| 20 | vinyl stearate ($C_{18}$ acid) | A | 113,300 | 21 | 230 | 14 | 18 |
| 21 | 1-hexadecene | C | 94,100 | 26 | 174 | 14 | 17 |

[1]All leathers were prepared according to procedure F, including the optional chrome post treatment (Step 8). The copolymers were charged at 6 wt % solids on the weight of the blue stock

TABLE 4

Amphiphilic Polymer Compositions with More than 2 Monomers

| Polymer[1] Composition CEMA | BA | AA | Polymer Synth. Process | Dynamic Water Reistance Maeser Flexes | Static Water Resistance wt % Uptake | Temper (mils) | Extensions Grain Crack | Ball Burst |
|---|---|---|---|---|---|---|---|---|
| Targets | | | | | | | | |
| fatliquored leather | | | | | | ≧155 | ≧13 | ≧15 |
| waterproof leather | | | | >15,000 | <30 | | | |
| water resistant leather | | | | >1,000 | <70 | | | |
| 70 | — | 30 | A | 63,900 | 23 | 208 | 16 | 18 |
| 55 | 20 | 25 | A | 10,000 | 23 | 196 | 13 | 18 |
| 50 | 30 | 20 | A | 1,400 | 28 | 190 | 14 | 18 |
| 40 | 40 | 20 | A | 1,900 | 36 | 174 | 13 | 17 |

[1]CEMA = a mixture of $C_{16}$, $C_{18}$ $C_{20}$ methacrylates,
BA = butyl acrylate,
AA = acrylic acid.

EXAMPLE 5: AMPHIPHILIC COPOLYMERS OF VARIOUS MOLECULAR WEIGHTS dure F, and were given the optional post treatment with chromium (Step 8).

TABLE 6

| | | Variations in the Hydrophilic Monomer | | | | | |
|---|---|---|---|---|---|---|---|
| Sample | Polymer[1] Comp. | Synth. Process | Temper (mils) | Extensions | | Dynamic Water Resistance | Static Water Resistance |
| | | | | Grain Crack | Ball Burst | Maeser Flexes | Wt % Uptake |
| | Targets | | ≧155 | ≧13 | ≧15 | | |
| | No polymer | (Ctrl) | 133 | 12 | 13 | 50 | 93 |
| 1 | acrylic acid | A | 201 | 16 | 18 | 94,800 | 25 |
| 2 | methacrylic acid | A | 194 | 16 | 18 | 1,900 | 31 |
| 3 | sulfoethyl methacrylate | B | 181 | 14 | 18 | 250 | 60 |
| 4 | phosphoethyl methacrylate | B | 161 | 14 | 15 | 3,200 | 36 |

[1])Compositions are all 70 wt % CEMA/30 wt % of the hydrophilic monomer shown.

Amphiphilic polymers covering a wide range of molecular weights may be used in practicing this invention. This is illustrated in Table 5. The polymers in Table 5 were prepared according to Process D. The leathers were treated according to Process F, including the optional post treatment with chrome (Step 8). All polymers confer improvements in water resistance and strength to the leather.

TABLE 5

| | Amphiphilic Copolymers of Various Molecular Weights | | | | |
|---|---|---|---|---|---|
| Polymer Molecular[1] Weight (Weight Average) | Dynamic Water Resistance Maeser Flexes | Static Water Resistance wt % Uptake | Temper (mils) | Extensions | |
| | | | | Grain Crack | Ball Burst |
| Targets | | | | | |
| fatliquored leather | | | ≧155 | ≧13 | ≧15 |
| waterproof leather | >15,000 | <30 | | | |
| water resistants leather | >1,000 | <70 | | | |
| 3,000 | 55,400 | 24 | 227 | 16 | 22 |
| 4,000 | 117,800 | 25 | 227 | 15 | 21 |
| 10,000 | 116,900 | 26 | 240 | 16 | 21 |
| 16,650 | 114,900 | 28 | 178 | 15 | 20 |
| 25,100 | 31,000 | 34 | 161 | 14 | 18 |
| 69,000 | 2,000 | 26 | 159 | 13 | 18 |

[1])All copolymers are 70 CEMA/30 AA in composition, prepared according to Process D. The molecular weights were determined by aqueous gel permeation chromatography on samples of polymer which were first hydrolyzed to a poly-AA-co-MAA backbone with ethanolic KOH and using polyacrylic acid standards of known molecular weight. The molecular weight results from the gel permeation chromatography of the pAA-co-MAA were then corrected to account for the weight of the ester side chains lost during the hydrolysis procedure.

EXAMPLE 6: OTHER HYDROPHILIC MONOMERS

Table 6 illustrates the treatment process using amphiphilic copolymer compositions prepared using various hydrophilic monomers. The copolymers were demonstrated to be effective, one treatment retan/fatliquors as shown by the strength parameters of the resulting leather. All leathers were treated according to Procedure F, and were given the optional post treatment with chromium (Step 8).

EXAMPLE 7: WASHABLE LEATHERS

Table 7 illustrates the advantages of using amphiphilic polymers over conventional fatliquors for making washable leathers. The leathers were washed in a toploading automatic washing machine using powdered Tide ® detergent. Both the leather treated with a conventional sulfated fatliquor (comparative) and the leathers treated with the amphiphilic copolymers of the invention retain a considerable degree of softness and strength, as indicated by the values for temper and elongation at grain crack and ball burst. Unlike the other two leathers, the leather prepared with the amphiphilic copolymers, which had been post treatment with chrome (Step 8), illustrated improvements in softness and strength. The leathers treated with the amphiphilic copolymer showed considerable advantage in the rates at which they dried after being washed. The leathers were air dried to simulate drying on a clothes line as is generally recommended for fine washables.

TABLE 7

THE USE OF AMPHIPHILIC COPOLYMERS AS FATLIQUORS FOR MAKING WASHABLE LEATHER

| Leather | (Process) | Fatliquor | Post Treatment (Step 8/11) |
|---|---|---|---|
| Comp A | (E) | 4.2 wt % Morite G-82 | 3% Tanolin ® M-1 |
| B | (F) | 4.0 wt % Amphiphilic Copolymer 70% CEMA/30% AA | none |
| C | (F) | 4.0 wt % Amphiphilic Copolymer 70% CEMA/30% AA | 3% Tanolin ® M-1 |

| | PERFORMANCE | | | | | | |
|---|---|---|---|---|---|---|---|
| | Temper[1] | | | Elongation[3] | | Drying Rate (% moisture)[4] | | |
| | Bef | Aft | Temper[2] | Grain Crack | Ball Burst | hours after washing | | |
| Leather | Washing | | Percent Change | bef/aft | bef/aft | 18 hr | 36 hr | 60 hr |

TABLE 7-continued

THE USE OF AMPHIPHILIC COPOLYMERS AS FATLIQUORS
FOR MAKING WASHABLE LEATHER

| A | 184 | 175 | −5   | 13 | 14 | 15 | 15 | >28      | 20 | 14 (dry) |
| B | 196 | 191 | −2.6 | 15 | 15 | 18 | 18 | 14 (dry) | 13 | 13       |
| C | 219 | 221 | +0.9 | 13 | 14 | 18 | 20 | 15 (dry) | 13 | 13       |

[1] bef = before washing; aft = after washing and air drying
[2] change in temper after one wash cycle
[3] bef = before washing; aft = after washing and air drying
[4] The drying rate was determined both quantitatively and qualitatively; the quantitative determination utilized a standard moisture meter to measure the % moisture in the leather as a function of time after the leather was removed from the washing machine. The leather is considered to be dry when the moisture content reaches 18% or less. The qualitative measure was to determine when the leather felt dry to the touch, such that wearing a garment of that leather would be comfortable. This is indicated in the table by the designation (dry).

EXAMPLE 8: MINERAL TANNING AGENT POST TREATMENT OF TREATED LEATHERS ventional leathers (see Table 1). The amphiphilic copolymer in this example was 30 AA/70 CEMA, used at a 6% offer.

TABLE 8

The use of Various Minerial Tanning Agents to Enhance
The Water Resistance of Leather Prepared with Amphiphilic Copolymer.

| Blue Stock | Mineral[1] Tanning Agent | Dynamic Water Resistance Maeser Flexes | Static Water Resistance Wt % Uptake | Temper (mils) | Extensions | |
|---|---|---|---|---|---|---|
| | | | | | Grain Crack | Ball Burst |
| Targets | | | | | | |
| waterproof leather | | >15,000 | ≦30 | ≧155 | ≧13 | ≧15 |
| water resistant leather | | >1,000 | ≦70 | ≧155 | ≧13 | ≧15 |
| 5 oz | none | 3,000 | 37.5 | 175 | 15 | 20 |
| 5 oz | chrome | 115,000 | 20.8 | 190 | 16 | 19 |
| 4 oz | chrome | 65,300 | 29.1 | 201 | 14 | 18 |
| 4 oz | aluminum | 101,500 | 32.2 | 204 | 15 | 18 |
| 4 oz | zirconium | 42,400 | 27.7 | 183 | 14 | 18 |

[1] The tanning metal used as a posttreatment in Step 8 of Process F was as follows:
Chrome was 3 wt % Tanolin ® M-1, from Hamblett and Hayes
Aluminum was 3 wt % aluminum sulfate
Zirconium was 3 wt % Zirc 33 ®, a commercial zero basicity zirconium sulfate tanning salt.

Table 8 illustrates the effects of posttreatment with various mineral tanning agents on the water resistance of leathers treated with the selected amphiphilic copolymers. Fixation of conventional fatliquors by a posttreatment with a tanning metal such as aluminum (Al), zirconium (Zr), chromium (Cr) or iron (Fe) is a known method of improving the water resistance of leather. See "Hydrophobing Leather", The Leather Manufacturer, May 1986, p 11–14;
U.S. Pat. No. 3,010,780 to Bohme Fettchemi G.m.b.H., Nov 28, 1961, and
"An Aqueous System for the Production of a Dry Cleanable Leather which is No Longer Wettable", Rev. Tech. Ind. Cuir, vol 69, issue 4,p. 107–111 (1977).

All leathers were prepared according to Procedure F, which included the optional post treatment (Step 8) as indicated. Even in the absence of the post treatment, leathers prepared with the amphiphilic copolymer are found to be substantially more water resistant than con-

EXAMPLE 9: RESISTANCE TO SOLVENT EXTRACTION

Table 9 illustrates the improved resistance to solvent extraction of leathers treated with the amphiphilic copolymer compared to leather prepared with a conventional fatliquor. Resistance to solvent extraction is an indicator of dry cleanability. The amphiphilic copolymer in this example was 70 CERA/30 AA used at 6% offer. The conventional fatliquor was Morite G-82, a sulfated oil, used at 4.2% offer. The optional post treatment with chrome was used where indicated. The leather was first dried for 4 hours at 100° C. It was then weighed and this weight of the dried leather was taken as the initial weight. The leather was placed in the cup of a Soxhlet Extractor and extracted for 10–12 hours with methylene chloride. The methylene chloride was then evaporated to determine the weight of solids extracted from the leather. The amount of material extracted is reported as a weight percent of the initial weight.

TABLE 9

Resistance to Extraction by Methylene Chloride
Amphiphilic Copolymer Versus a Conventional Fatliquor

| | Fatliquor | Leather Making Process | Posttreatment with chrome | Wt % Extractables Based on Initial Weight of Leather |
|---|---|---|---|---|
| Control | none | N/A | none | (approx.) 0.5 |
| Control | none | N/A | 3% Tanolin ® M-1 | 1.0 |
| Comp. | G-82 | Process E | none | 2.4 |
| Comp. | G-82 | Process E | 3% Tanolin ® M-1 | 2.4 |
| | Amphiphilic Copolymer | Process F | none | 1.3 |
| | Amphiphilic | Process F | 3% Tanolin ® M-1 | 1.0 |

TABLE 9-continued

Resistance to Extraction by Methylene Chloride
Amphiphilic Copolymer Versus a Conventional Fatliquor

| Fatliquor | Leather Making Process | Posttreatment with chrome | Wt % Extractables Based on Initial Weight of Leather |
|---|---|---|---|
| Copolymer | | | |

EXAMPLE 10: DRYING IMPROVEMENT

At the end of the wet end processing the leather is dried. Leathers treated with the amphiphilic copolymers were found to dry more readily than leathers treated with conventional fatliquors. This offers a savings in both time and in the energy required to dry the leather. The more rapid drying rate of leather fatliquored with the amphiphilic copolymer is illustrated in Table 10. In this example, the leather was prepared according to Procedure E or F up to the last step. After the final wash, the leather was horsed overnight and then toggle air dried at room temperature. The Table shows the wt % moisture in the leather versus time of toggle drying. Leather is considered to be dry and ready for staking when the moisture content reaches 18%. Extrapolation of the data in Table 10 gives a toggle air dry time of 12 hours for conventionally treated leather versus 8 hours for leather treated with the amphiphilic copolymer.

TABLE 10

| Fatliquor | Drying Rate of Leathers | | | |
|---|---|---|---|---|
| | Morite G-82 | | Amphiphilic Copolymer | |
| Posttreatment | 3% chrome | none | 3% chrome | none |
| Drying Time | Percent Moisture in the Leather | | | |
| initial | ≈50 | ≈50 | ≈50 | ≈50 |
| 5 hrs | 27 | 28 | 23 | 26 |
| 6 hrs | 26 | 26 | 19 | 21 |
| 15 hrs | 17 | 17 | 14 | 14 |
| 72 hrs | 17 | 17 | 14 | 14 |

What is claimed is:

1. A method for improving the properties of tanned leather comprising treating said tanned leather with at least one weight percent of an aqueous dispersion comprising a water insoluble dispersed amphiphilic copolymer formed from about 52 weight percent to about 88 weight percent to of at least one hydrophobic monomer selected from the group consisting of long chain alkyl (meth)acrylates, long chain alkoxy- or alkylphenoxy (poly ethylene oxide) (meth)acrylates, primary alkenes, vinylesters of long chain alkyl carboxylic acids and mixtures thereof, said long chain alkyl groups containing at least 6 carbon atoms, with from about 12 weight percent to about 48 weight percent of at least one copolymerizable water soluble ethylenically unsaturated acidic or basic hydrophilic comonomer, and where said hydrophilic comonomer is other than methacrylic acid when said hydrophobic monomer is 2-ethylhexyl acrylate, and where said amphiphilic copolymer has a weight average molecular weight of from about 2000 to about 100,000, and where the treated has a temper of at least 155 mils and a dynamic water resistance greater than 1000 Maeser flexes.

2. The method of claim 1 wherein said hydrophilic comonomer used to prepare said amphiphilic copolymer is selected from the group consisting of acrylic acid, methacrylic acid, itaconic acid, fumaric acid, maleic acid and anhydrides of said diacids, acid substituted (meth)acrylates and (meth)acrylamides, amine substituted (meth)acrylates and (meth)acrylamides, and mixtures thereof.

3. The method of claim 1 further comprising post treating the amphiphilic copolymer treated leather with a mineral tanning agent.

4. The method of claim 3 wherein said mineral tanning agent is selected from the group consisting of chromium, aluminum and zirconium tanning agents.

5. The leather produced by the process of claim 1.

6. A method for making tanned leather waterproof comprising applying to a tanned leather an aqueous dispersion of an amphiphilic copolymer, the concentration of said amphiphilic copolymer being at least about 1 percent on the weight of said tanned leather, said amphiphilic copolymer being formed from about 52 weight percent to about 88 weight percent of at least one hydrophobic monomer selected from the group consisting of long chain alkyl (meth)acrylates, long chain alkoxy- or alkylphenoxy (poly ethylene oxide) (meth)acrylates, vinylesters of long chain alkyl carboxylic acids and mixtures thereof, said long chain alkyl groups containing at least 6 carbon atoms, with from about 12 weight percent to about 48 weight percent of at least one copolymerizable water soluble ethylenically unsaturated acidic hydrophilic comonomer, and wherein said hydrophilic comonomer is other than methacrylic acid when said hydrophobic monomer is 2-ethylhexyl acrylate, and where said amphiphilic copolymer has a weight average molecular weight of from about 2000 to about 100,000, and post treating said leather with a mineral tanning agent, and where the treated and post treated leather has a dynamic water resistance greater than 15000 Maeser flexes.

7. A method of claim 6 wherein the mineral tanning agent is selected from the group consisting of chrome, aluminum and zironcium tanning agents.

8. The method of claims 1 or 6 wherein said amphiphilic copolymer is formed from about 55 to about 85 percent by weight of said hydrophobic comonomer and from about 15 to about 45 percent by weight of said hydrophilic comonomer.

9. The method of claims 1 or 6 wherein said amphiphilic copolymers is formed from 60 to about 80 percent by weight of said hydrophobic comonomer and from about 20 to about 40 percent by weight of said hydrophilic commoner.

10. The leather produced by the process of claim 6.

11. A method for wet end processing of hides or skins to form leather comprising tanning the hide or skin with a conventional tanning agent and applying to said tanned hide or skin at least one weight percent of an aqueous dispersion comprising a water insoluble dispersed amphiphilic copolymer formed from about 52 weight percent to about 88 weight percent of at least one hydrophobic monomer selected from the group consisting of long chain alkyl (meth)acrylates, long chain alkoxy- or alkylphenoxy (poly ethylene oxide) (meth)acrylates, primary alkenes, vinylesters of long chain alkyl carboxylic acids and mixtures thereof, said long chain alkyl groups containing at least 6 carbon atoms, with from about 12 weight percent to about 48 weight percent of at least one copolymerizable water soluble ethylenically unsaturated acidic or basic hydrophilic comonomer, and where said hydrophilic comonomer is other than methacrylic acid when said hydrophobic monomer is 2-ethylhexyl acrylate, and where said amphiphilic copolymer has a weight average molecular weight of from about 2000 to about 100,000, and where the treated leather has a temper of at least 155 mils and a dynamic water resistance greater than 1000 Maeser flexes.

12. The leather produced by the process of claim 11.

13. A method for making leather water resistant, which comprises treating tanned leather with at least 1% by weight of an aqueous dispersion comprising a water insoluble dispersed amphiphilic copolymer formed from
   (a) about 52% to about 88% by weight of at least one hydrophobic comonomer selected from the group consisting of $C_8$–$C_{22}$-alkyl acrylates, $C_8$–$C_{22}$-alkyl methacrylates, $C_8$–$C_{22}$-alkoxy- or $C_6$–$C_{12}$-alkylphenoxy(poly ethylene oxide) (meth)acrylates and vinyl esters of $C_{12}$–$C_{22}$-alkyl carboxylic acids and
   (b) about 12% to about 48% by weight of at least one water soluble ethylenically unsaturated acidic or basic hydrophilic comonomer, wherein said hydrophilic comonomer is other than methacrylic acid when said hydrophobic monomer is 2-ethylhexyl acrylate, and wherein said copolymer has a molecular mass of from about 2,000 to 100,000 weight average molecular weight.

14. A method for making tanned leather waterproof comprising applying to a tanned leather an aqueous dispersion of an amphiphilic copolymer, the concentration of said amphiphilic copolymer being at least about 1 percent on the weight of said tanned leather, said amphiphilic copolymer being formed from about 52 weight percent to about 88 weight percent of at least one hydrophobic monomer selected from the group consisting of long chain alkyl (meth)acrylates, long chain alkoxy- or alkylphenoxy (poly ethylene oxide) (meth)acrylates, primary alkenes, vinylesters of long chain alkyl carboxylic acids and mixtures thereof, said long chain alkyl groups containing at least 6 carbon atoms, with from about 12 weight percent to about 48 weight percent of at least one copolymerizable water soluble ethylenically unsaturated basic hydrophilic comonomer, and where said hydrophilic comonomer is other than methacrylic acid when said hydrophobic monomer is 2-ethylhexyl acrylate, and where said amphiphilic copolymer has a weight average molecular weight of from about 2000 to about 100,000, and post treating said leather with a mineral tanning agent, and where the treated and post treated leather has a dynamic water resistance greater than 15000 Maeser flexes.

* * * * *